US012714989B2

(12) United States Patent
Xing et al.

(10) Patent No.: US 12,714,989 B2
(45) Date of Patent: Aug. 25, 2026

(54) METAL-ORGANIC FRAMEWORK (MOF) MIL-125 AND PREPARATION METHOD AND USE THEREOF

(71) Applicant: DALIAN INSTITUTE OF CHEMICAL PHYSICS, CHINESE ACADEMY OF SCIENCES, Dalian (CN)

(72) Inventors: Jiacheng Xing, Dalian (CN); Liping Yang, Dalian (CN); Danhua Yuan, Dalian (CN); Yunpeng Xu, Dalian (CN); Zhongmin Liu, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 790 days.

(21) Appl. No.: 18/025,660

(22) PCT Filed: Sep. 11, 2020

(86) PCT No.: PCT/CN2020/114895
§ 371 (c)(1),
(2) Date: Mar. 10, 2023

(87) PCT Pub. No.: WO2022/052067
PCT Pub. Date: Mar. 17, 2022

(65) Prior Publication Data

US 2023/0338935 A1 Oct. 26, 2023

(51) Int. Cl.

| | |
|---|---|
| ***B01J 31/16*** | (2006.01) |
| ***B01J 35/40*** | (2024.01) |
| ***B01J 35/50*** | (2024.01) |
| ***B01J 35/61*** | (2024.01) |
| ***B01J 35/64*** | (2024.01) |
| ***B01J 37/03*** | (2006.01) |
| ***B01J 37/04*** | (2006.01) |
| ***C07D 301/19*** | (2006.01) |
| ***C07F 7/28*** | (2006.01) |

(52) U.S. Cl.
CPC ........... *B01J 31/1691* (2013.01); *B01J 35/40* (2024.01); *B01J 35/50* (2024.01); *B01J 35/615* (2024.01); *B01J 35/617* (2024.01); *B01J 35/618* (2024.01); *B01J 35/643* (2024.01); *B01J 37/031* (2013.01); *B01J 37/04* (2013.01); *C07D 301/19* (2013.01); *C07F 7/28* (2013.01); *B01J 2231/72* (2013.01); *B01J 2235/15* (2024.01); *B01J 2235/30* (2024.01); *B01J 2531/004* (2013.01); *B01J 2531/46* (2013.01)

(58) Field of Classification Search
None
See application file for complete search history.

(56) References Cited

U.S. PATENT DOCUMENTS

2016/0064772 A1 3/2016 Choi et al.

FOREIGN PATENT DOCUMENTS

| | | | |
|---|---|---|---|
| CN | 102928474 | A | 2/2013 |
| CN | 106824280 | A | 6/2017 |
| CN | 109331881 | A | 2/2019 |
| CN | 111186843 | A | 5/2020 |
| CN | 111430640 | A | 7/2020 |

OTHER PUBLICATIONS

Yang. Dalton Transactions, 2020, 49, 10052-10057, electronic supplementary information table 1 and figures S1-S8 (Year: 2020).*
McNamara. ACS Applied Materials and Interfaces, Jul. 2015, 5338-5346, supporting information pp. S1-S15 (Year: 2015).*
Machine translation of CN 111430640, published Jul. 17, 2020. (Year: 2020).*
Nataliya Maksimchuk, et al., Cyclohexene Oxidation with H2O2 over: Metal-Organic Framework MIL-125(Ti): The Effect of Protons on Reactivity, Catalysts, 2019, pp. 1-14, vol. 9, No. 324.
Jiacheng Xing, et al., Synthesis of Titanium Silicon Molecular Sieve TS-1 Having High Catalytic Oxidation Performance and No Non-Skeletal Titanium Using New Ti—Si Polymer, The 19th National Conference on Catalysis (Chongqing) Synthesis, 2019.

* cited by examiner

*Primary Examiner* — Noble E Jarrell
(74) *Attorney, Agent, or Firm* — Bayramoglu Law Offices LLC

(57) ABSTRACT

A metal-organic framework (MOF) MIL-125 and a preparation method and a use thereof are provided. The MOF MIL-125 is a round cake-like crystal and has an external specific surface area (SSA) of 160 $m^2/g$ to 220 $m^2/g$. The MOF MIL-125 provided in the present application has a large number of microporous structures, a large external SSA, and a high catalytic activity in oxidation.

17 Claims, 2 Drawing Sheets

METAL-ORGANIC FRAMEWORK (MOF) MIL-125 AND PREPARATION METHOD AND USE THEREOF

CROSS REFERENCE TO THE RELATED APPLICATIONS

This application is the national phase entry of International Application No. PCT/CN2020/114895, filed on Sep. 11, 2020, the entire contents of which are incorporated herein by reference.

TECHNICAL FIELD

The present application relates to a metal-organic framework (MOF) MIL-125 and a preparation method and a use thereof and belongs to the field of material preparation.

BACKGROUND

The MOF MIL-125 is a typical titanium-containing MOF, is the first titanium-doped carboxylic acid complex with a crystal structure and a pore structure and is widely used in photocatalytic oxidation and adsorptive separation.

At present, there are great difficulties in the synthesis of the MOF MIL-125 because a titanium source is easily hydrolyzed and the hydrolysis rate thereof during synthesis is difficult to control. Therefore, in the current synthesis methods, it is necessary to strictly remove water during a synthesis process, and most operations need to be conducted in a glove box, which seriously affects the application and industrial scale-up of the MOF MIL-125.

In addition, the MOF MIL-125 is a typical microporous material with many catalytic active sites and prominent catalytic oxidation performance and has important applications in a reaction system in which tert-butyl hydroperoxide or hydrogen peroxide is used as an oxidizing agent for catalytic oxidation of cyclohexene.

SUMMARY

The present application is intended to provide a titanium-containing MOF MIL-125, which has a large number of microporous structures, a large external specific surface area (SSA), and a high catalytic activity in oxidation.

According to a first aspect of the present application, an MOF MIL-125 is provided, and the MOF MIL-125 is a round cake-like crystal and has an external SSA of 160 $m^2/g$ to 220 $m^2/g$.

Optionally, a mass content of particles with a particle size of 1.6 μm to 1.8 μm in the MOF MIL-125 is 85% to 95%.

Specifically, the external SSA of the MOF MIL-125 provided in the present application is as high as 236 $m^3/g$ and is much larger than an external SSA (91 $m^3/g$ to 98 $m^3/g$) of the traditional MOF MIL-125, which reduces the mass transfer resistance, increases the reaction-diffusion path, is conducive to the diffusion of reaction raw materials and products, and improves the reaction conversion rate.

Specifically, the MOF MIL-125 in the present application has a regular morphology and a uniform size, while the traditional MOF MIL-125 is fragmented and has an extremely uneven particle size distribution and an irregular morphology.

Optionally, the MOF MIL-125 includes a micropore with an SSA of 1,000 $m^2/g$ to 1,500 $m^2/g$.

Optionally, the MOF MIL-125 includes a micropore with an SSA of 1,200 $m^2/g$ to 1,300 $m^2/g$.

Optionally, the microporous MOF MIL-125 has a large micropore area.

Optionally, the MOF MIL-125 has a particle size of 1.6 μm to 1.8 μm.

According to a second aspect of the present application, a preparation method of the MOF MIL-125 described above is provided, including: preparing the MOF MIL-125 with a titanium-ester polymer as a titanium source.

In particular, the titanium-ester polymer in the present application is obtained by linking a titanium source to a same polymer.

Optionally, the preparation method includes: subjecting a mixture of the titanium-ester polymer, an organic ligand, and an organic solvent to crystallization to obtain the MOF MIL-125, where the organic ligand is terephthalic acid; and the crystallization refers to solvothermal crystallization.

Specifically, the present application provides a titanium source that is insoluble in water and unhydrolyzed, that is, the titanium-ester polymer is insoluble in water and unhydrolyzed. Therefore, in a process of synthesizing the MOF MIL-125, there is no need for strict water removal, and there will be no precipitation of titanium dioxide, such that the mass production of the MOF MIL-125 can be realized, which is suitable for industrial applications.

Optionally, the preparation method of the MOF MIL-125 in the present application includes:

a) thoroughly mixing a titanate and a polyol, introducing nitrogen for protection, and subjecting a resulting mixture to a transesterification reaction for 2 h to 10 h at 80° C. to 180° C. under stirring;

b) subjecting a reaction system obtained in step a) to vacuum distillation for 0.5 h to 5 h at a vacuum degree of 0.01 KPa to 5 KPa and a temperature of 170° C. to 230° C. to obtain the titanium-ester polymer;

c) mixing the titanium-ester polymer obtained in step b) with the terephthalic acid and the organic solvent, and stirring a resulting mixture for 0 h to 100 h at a temperature not higher than 120° C. to obtain a gel mixture; and d) heating the gel mixture obtained in step c) under closed conditions to 100° C. to 200° C., and conducting crystallization for 0 d to 30 d at an autogenous pressure to obtain the microporous MOF MIL-125.

Optionally, the crystallization is conducted in a dynamic or static state. Optionally, after the crystallization is completed, a solid product is separated, washed until neutral, and dried to obtain the MOF MIL-125.

Optionally, the titanium-ester polymer is obtained by subjecting a raw material including a titanate and a polyol to a transesterification reaction.

Optionally, the transesterification reaction is conducted under stirring.

Optionally, the transesterification reaction is conducted for 2 h to 10 h at 80° C. to 180° C. in an inert atmosphere.

Optionally, an upper limit of the temperature for the transesterification reaction is selected from the group consisting of 85° C., 90° C., 100° C., 110° C., 120° C., 130° C., 140° C., 150° C., 160° C., 170° C., 175° C., and 180° C.; and a lower limit of the temperature for the transesterification reaction is selected from the group consisting of 80° C., 85° C., 90° C., 100° C., 110° C., 120° C., 130° C., 140° C., 150° C., 160° C., 170° C., and 175° C.

Optionally, an upper limit of the reaction time for the transesterification reaction is selected from the group consisting of 2.5 h, 3 h, 4 h, 5 h, 6 h, 7 h, 8 h, 9 h, 9.5 h, and 10 h; and a lower limit of the reaction time for the transesterification reaction is selected from the group consisting of 2 h, 2.5 h, 3 h, 4 h, 5 h, 6 h, 7 h, 8 h, 9 h, and 9.5 h.

Optionally, the transesterification reaction is conducted for 2 h to 10 h at 80° C. to 180° C. under nitrogen protection.

Optionally, the transesterification reaction is conducted for 2 h to 10 h at 100° C. to 160° C. in an inert atmosphere.

Optionally, the transesterification reaction is conducted for 4 h to 8 h at 100° C. to 160° C. in an inert atmosphere.

Optionally, the transesterification reaction is conducted for 4 h to 8 h at 100° C. to 160° C. under nitrogen protection.

Optionally, the inert atmosphere includes at least one selected from the group consisting of nitrogen and an inert gas.

Optionally, a conversion rate of the transesterification reaction is 60% to 80%.

Optionally, a conversion rate of the transesterification reaction is not greater than 90%.

Optionally, the transesterification reaction further includes vacuum distillation.

Optionally, the vacuum distillation is conducted for 0.5 h to 5 h at a temperature of 170° C. to 230° C. and a vacuum degree of 0.01 KPa to 5 KPa.

Optionally, the vacuum degree is 0.05 Kpa to 3 Kpa.

Optionally, an upper limit of the temperature for the vacuum distillation is selected from the group consisting of 175° C., 180° C., 190° C., 200° C., 210° C., 220° C., 225° C., and 230° C.; and a lower limit of the temperature for the vacuum distillation is selected from the group consisting of 170° C., 175° C., 180° C., 190° C., 200° C., 210° C., 220° C., and 225° C.

Optionally, an upper limit of the time for the vacuum distillation is selected from the group consisting of 0.8 h, 1 h, 2 h, 3 h, 4 h, 4.5 h, and 5 h; and a lower limit of the time for the vacuum distillation is selected from the group consisting of 0.5 h, 0.8 h, 1 h, 2 h, 3 h, 4 h, and 4.5 h.

Optionally, an upper limit of the vacuum degree for the vacuum distillation is selected from the group consisting of 0.02 KPa, 0.03 Kpa, 0.05 KPa, 0.08 Kpa, 0.1 KPa, 0.5 KPa, 1 KPa, 1.5 KPa, 2 KPa, 2.5 KPa, 3 KPa, 3.5 KPa, 4 KPa, 4.5 KPa, and 5 KPa; and a lower limit of the vacuum degree for the vacuum distillation is selected from the group consisting of 0.01 KPa, 0.02 KPa, 0.03 KPa, 0.05 KPa, 0.08 KPa, 0.1 KPa, 0.5 KPa, 1 KPa, 1.5 KPa, 2 KPa, 2.5 KPa, 3 KPa, 3.5 KPa, 4 KPa, and 4.5 KPa.

Optionally, a molar ratio of the titanate to the polyol meets the following condition:

$$\text{titanate:polyol}=(0.5-5)x:4$$

where x represents a mole number of hydroxyl in each mole of the polyol; and a mole number of each of the above substances refers to a mole number of the substance itself.

Optionally, a molar ratio of the titanate to the polyol meets the following condition:

$$\text{titanate:polyol}=(0.8-1.2)x:4$$

where x represents a mole number of hydroxyl in each mole of the polyol; and a mole number of each of the above substances refers to a mole number of the substance itself.

Optionally, an upper limit of the molar ratio of the titanate to the polyol is selected from the group consisting of 0.85 x:4, 0.9 x:4, 0.95 x:4, 1.0 x:4, 1.15 x:4, and 1.2 x:4; and a lower limit of the molar ratio of the titanate to the polyol is selected from the group consisting of 0.8 x:4, 0.85 x:4, 0.9 x:4, 0.95 x:4, 1.0 x:4, and 1.15 x:4, where x represents a mole number of hydroxyl in each mole of the polyol.

Optionally, the titanate is at least one selected from the group consisting of compounds with a chemical formula shown in formula II:

formula II

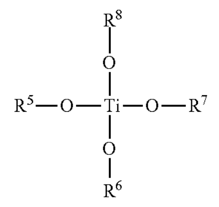

where $R^5$, $R^6$, $R^7$, and $R^8$ each are independently selected from the group consisting of $C_1$-$C_{10}$ alkyl groups.

Optionally, $R^5$, $R^6$, $R^7$, and $R^8$ in formula II each are independently selected from the group consisting of $C_1$-$C_4$ alkyl groups.

Optionally, the titanate includes at least one selected from the group consisting of tetraethyl titanate, tetraisopropyl titanate (TIPT), tetrabutyl titanate, tetrahexyl titanate, and tetraisooctyl titanate.

Optionally, the titanate is one or more selected from the group consisting of tetraethyl titanate, TIPT, tetrabutyl titanate, tetrahexyl titanate, and tetraisooctyl titanate.

Optionally, the polyol includes at least one selected from the group consisting of ethylene glycol (EG), diethylene glycol (DEG), triethylene glycol (TEG), tetraethylene glycol, 1,2-propanediol, 1,3-propanediol, 1,4-butanediol, 1,6-hexanediol, polyethylene glycol (PEG) 200, PEG 400, PEG 600, PEG 800, 1,4-cyclohexanediol, 1,4-cyclohexanedimethanol (1,4-CHDM), 1,4-benzenedimethanol, glycerol, trimethylolpropane, pentaerythritol, xylitol, and sorbitol.

Optionally, the polyol has 2 or more hydroxyl groups; and the polyol includes any one or a mixture of two or more selected from the group consisting of EG, DEG, TEG, tetraethylene glycol, 1,2-propanediol, 1,3-propanediol, 1,4-butanediol, 1,6-hexanediol, PEG 200, PEG 400, PEG 600, PEG 800, 1,4-cyclohexanediol, 1,4-CHDM, 1,4-benzenedimethanol, glycerol, trimethylolpropane, pentaerythritol, xylitol, and sorbitol.

Optionally, the titanium-ester polymer includes at least one selected from the group consisting of a titanium-PEG ester polymer, a titanium-EG ester polymer, and a titanium-1,4-benzenedimethanol ester polymer.

Optionally, the crystallization is conducted for no more than 30 d at a temperature of 100° C. to 200° C. and an autogenous pressure under closed conditions.

Optionally, an upper limit of the temperature for the crystallization is selected from the group consisting of 110° C., 120° C., 130° C., 140° C., 150° C., 160° C., 170° C., 180° C., 190° C., and 200° C.; and a lower limit of the temperature for the crystallization is selected from the group consisting of 100° C., 110° C., 120° C., 130° C., 140° C., 150° C., 160° C., 170° C., 180° C., and 190° C.

Optionally, an upper limit of the time for the crystallization is selected from the group consisting of 1 h, 5 h, 10 h, 15 h, 20 h, 1 d, 2 d, 5 d, 10 d, 12 d, 15 d, 20 d, 25 d, 28 d, and 30 d; and a lower limit of the time for the crystallization is selected from the group consisting of 0.5 h, 1 h, 5 h, 10 h, 15 h, 20 h, 1 d, 2 d, 5 d, 10 d, 12 d, 15 d, 20 d, 25 d, and 28 d.

Preferably, the crystallization is conducted for 1 d to 15 d at a temperature of 120° C. to 180° C. and an autogenous pressure under closed conditions.

Optionally, a molar ratio of the titanium-ester polymer to the organic ligand is (0.5-2):1;

a mole number of the titanium-ester polymer is calculated based on a titanium content in the titanium-ester polymer; and the titanium content in the titanium-ester polymer is calculated based on a mole number of $TiO_2$.

Optionally, an upper limit of the molar ratio of the titanium-ester polymer to the terephthalic acid is selected from the group consisting of 0.55, 0.6, 0.65, 0.7, 0.75, 0.8, 0.82, 0.84, 0.86, 0.88, 0.92, 0.94, 0.96, 0.98, 1.2, 1.5, 1.6, 1.8, 1.9, and 2.0; and a lower limit of the molar ratio of the titanium-ester polymer to the terephthalic acid is selected from the group consisting of 0.5, 0.55, 0.6, 0.65, 0.7, 0.75, 0.8, 0.82, 0.84, 0.86, 0.88, 0.92, 0.94, 0.96, 0.98, 1.2, 1.5, 1.6, 1.8, and 1.9. A mole number of the titanium-ester polymer is calculated based on a titanium content in the titanium-ester polymer; and the titanium content in the titanium-ester polymer is calculated based on a mole number of $TiO_2$.

Optionally, the organic solvent is at least one selected from the group consisting of N,N-dimethylformamide (DMF) and methanol.

Optionally, the organic solvent includes DMF and methanol, and a volume ratio of the DMF to the methanol is (6-15):1.

Optionally, an upper limit of the volume ratio of the DMF to the methanol is selected from the group consisting of 6.2, 6.5, 7.0, 7.5, 8.0, 8.5, 9.0, 9.5, 10.5, 11.0, 12.0, 13.0, 14.0, and 15.0; and a lower limit of the volume ratio of the DMF to the methanol is selected from the group consisting of 6.0, 6.2, 6.5, 7.0, 7.5, 8.0, 8.5, 9.0, 9.5, 10.5, 11.0, 12.0, 13.0, and 14.0.

Optionally, the titanium-ester polymer is prepared by subjecting a titanate and a polyol to a transesterification reaction.

As a specific embodiment, the preparation method of the MOF MIL-125 includes:

a') thoroughly mixing a titanate and a polyol in a three-necked flask, connecting the three-necked flask to a distillation device, introducing nitrogen for protection, and subjecting a resulting mixture to a transesterification reaction for 2 h to 10 h at 80° C. to 180° C. under stirring, where a conversion rate of the transesterification reaction is 60% to 80%;

b') connecting the device obtained after the reaction in step a') to a water pump or oil pump, and subjecting a resulting reaction system to vacuum distillation for 0.5 h to 5 h at a vacuum degree of 0.01 KPa to 5 KPa and a temperature of 170° C. to 230° C. to make the transesterification reaction more complete to obtain the titanium-ester polymer, where a conversion rate of the transesterification reaction is greater than 90%;

c') mixing the titanium-ester polymer obtained in step b') with the terephthalic acid and the organic solvent, and stirring a resulting mixture for 0 h to 100 h at a temperature not higher than 120° C. to obtain a gel mixture;

d') placing the gel mixture obtained in step c') in a high-pressure reactor, sealing, heating to 100° C. to 200° C., and conducting crystallization for 0 d to 30 d at an autogenous pressure; and e') after the crystallization is completed, separating a solid product, washing with deionized water until neutral, and drying to obtain the MOF MIL-125.

As a specific embodiment, a preparation method of the titanium-ester polymer includes:

1) thoroughly mixing a titanate and a polyol in a three-necked flask, connecting the three-necked flask to a distillation device, introducing nitrogen for protection, and subjecting a resulting mixture to a transesterification reaction for 2 h to 10 h at 80° C. to 180° C. under stirring, where a conversion rate of the transesterification reaction is 60% to 80%; and 2) connecting the device obtained after the reaction in step 1) to a water pump or oil pump, and subjecting a resulting reaction system to vacuum distillation for 0.5 h to 5 h at a vacuum degree of 0.01 KPa to 5 KPa and a temperature of 170° C. to 230° C. to make the transesterification reaction more complete to obtain the titanium-ester polymer, where a conversion rate of the transesterification reaction is greater than 90%.

The synthesis process of the titanium-containing microporous MOF MIL-125 of the present application includes the following two steps: step 1: subjecting a mixture of a titanate and a polyol to a transesterification reaction, and distilling the generated alcohol out to obtain the titanium-ester polymer; and step 2: subjecting a mixture of the titanium-ester polymer, terephthalic acid, and an organic solvent to solvothermal crystallization in a reactor to obtain the titanium-containing microporous MOF MIL-125. In this method, a titanium source is linked to a same polymer to obtain the titanium-ester polymer, which can prevent the precipitation of $TiO_2$, involves a simple synthesis process, and does not require the operation in a glove box and the water removal during the traditional synthesis process. In addition, the MOF MIL-125 synthesized by this method has a large number of microporous structures, and thus exhibits high catalytic activity in oxidation.

Optionally, the titanium-containing microporous MOF MIL-125 prepared according to the method described above is used for selective oxidation of an organic matter including $H_2O_2$ and tert-butyl hydroperoxide.

According to a third aspect of the present application, a preparation method of epoxycyclohexane is provided, including subjecting a raw material including a compound A and cyclohexene to a reaction in the presence of an MOF MIL-125 to obtain the epoxycyclohexane, where the compound A is at least one selected from the group consisting of hydrogen peroxide and tert-butyl hydroperoxide; and the MOF MIL-125 is any one selected from the group consisting of the MOF MIL-125 described above and an MOF MIL-125 prepared by the preparation method described above.

Optionally, the compound A, the cyclohexene, and the MOF MIL-125 are in a mass ratio of (0.3-1.0):(0.3-1.2):(0.05-0.1).

Optionally, the reaction is conducted at 35° C. to 80° C. for 2 h to 8 h.

Optionally, the preparation method includes: subjecting a mixture including the MOF MIL-125, a solvent, the cyclohexene, and the compound A to a reaction to obtain the epoxycyclohexane.

Optionally, the compound A has a concentration of 30% to 55%.

Optionally, the solvent is at least one selected from the group consisting of methanol and DMF.

Optionally, the reaction is conducted in a water bath.

In the present application, "$C_1$-$C_{10}$", "$C_1$-$C_4$", or the like refers to a number of carbon atoms in a group.

In the present application, the "alkyl group" is a group obtained by removing any hydrogen atom on an alkane molecule.

In the present application, the external SSA refers to an SSA of a porous substance determined by a t-Plot method during the determination of physical adsorption, that is, a total Brunauer-Emmett-Teller (BET) area of the material minuses an SSA of micropores.

Possible beneficial effects of the present application:

The MOF MIL-125 provided by the present application has a regular morphology, a regular round cake shape, a uniform size, a large number of microporous structures, and a large external SSA, which can effectively reduce the mass transfer resistance, is conducive to the diffusion of products and reactants during reaction, and leads to high catalytic activity in oxidation. In the preparation method, a titanium source is linked to a same polymer to obtain a titanium-ester polymer that is unhydrolyzed and insoluble in water, which can prevent the precipitation of $TiO_2$, involves a simple synthesis process, and does not require the operation in a glove box and the water removal during the traditional synthesis process.

DETAILED DESCRIPTION OF THE EMBODIMENTS

Figure 1:
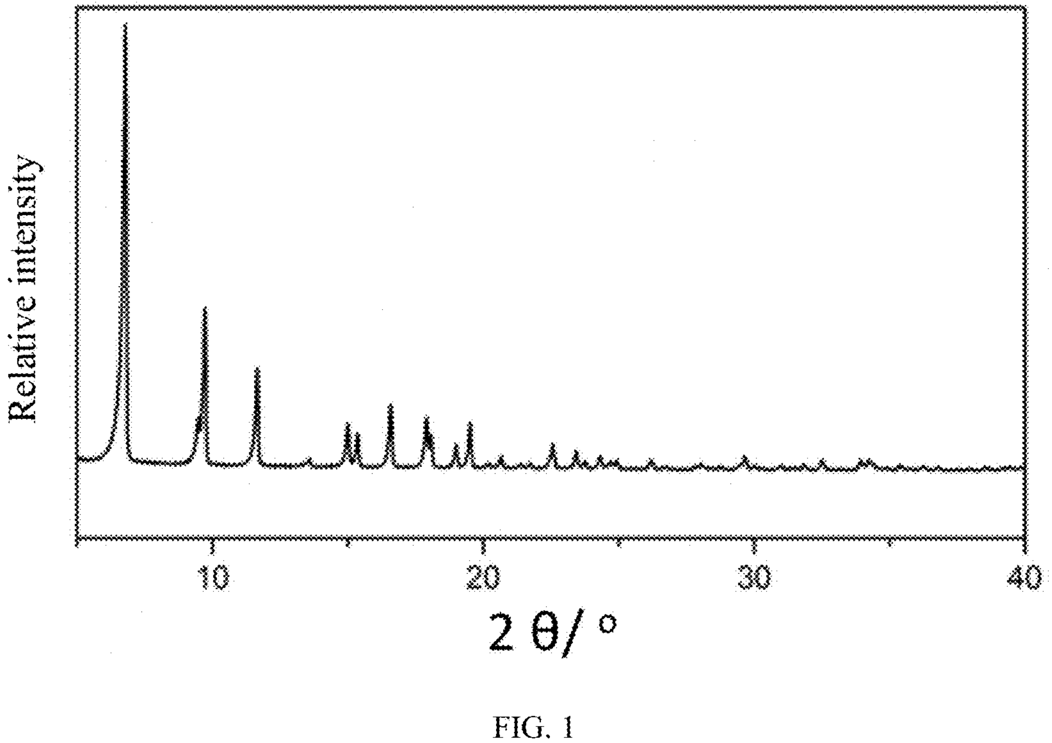
FIG. 1 is an X-ray diffractometry (XRD) pattern of the product synthesized in Example 1 of the present disclosure.

The present application will be described in detail below with reference to examples, but the present application is not limited to these examples.

Unless otherwise specified, the raw materials in the examples of the present application are all purchased from commercial sources.

In the examples of the present application, XRD of a product is conducted by an X'Pert PRO X-ray diffractometer of Netherlandish PANalytical under the following conditions: Cu target, Kα radiation source (λ=0.15418 nm), voltage: 40 KV, and current: 40 mA.

In the examples of the present application, the SEM of a product is conducted by an SU8020 scanning electron microscope of Hitachi.

In the examples of the present application, the physical adsorption and pore distribution of a product are analyzed by an ASAP2020 automatic physical instrument of Micromeritics.

In the examples of the present application, a particle size distribution of a product is analyzed by a ParticleTrack G600B particle size analyzer of METTLER TOLEDO.

In the examples of the present application, a conversion rate of a transesterification reaction is calculated in the following way:

According to a mole number n of alcohol distilled during the reaction, a number of groups participating in the transesterification reaction is determined to be n, and a total mole number of the titanate in the reaction raw material is m, such that the conversion rate of the transesterification reaction is: n/4 m.

According to an embodiment of the present application, a preparation method of an MOF MIL-125 includes:

a) a titanate and a polyol are thoroughly mixed in a three-necked flask, the three-necked flask is connected to a distillation device, nitrogen is introduced for protection, and a resulting mixture is subjected to a transesterification reaction for 2 h to 10 h at 80° C. to 180° C. under stirring, where a conversion rate of the transesterification reaction is 60% to 80%;

b) the device obtained after the reaction in step a) is connected to a water pump or oil pump, and a resulting reaction system is subjected to vacuum distillation for 0.5 h to 5 h at a vacuum degree of 0.01 KPa to 5 KPa and a temperature of 170° C. to 230° C. to make the transesterification reaction more complete to obtain the titanium-ester polymer, where a conversion rate of the transesterification reaction is greater than 90%;

c) the titanium-ester polymer obtained in step b) is mixed with the terephthalic acid and the organic solvent, and a resulting mixture is stirred or allowed to stand for 0 h to 100 h at a temperature not higher than 120° C. to obtain a gel mixture;

d) the gel mixture obtained in step c) is placed in a high-pressure reactor, the high-pressure reactor is sealed, and the gel mixture is heated to 100° C. to 200° C. and then subjected to crystallization for 0 d to 30 d at an autogenous pressure; and e) after the crystallization is completed, a solid product is separated, washed with deionized water until neutral, and dried to obtain the microporous MOF MIL-125.

The titanate in step a) is one or more selected from the group consisting of tetraethyl titanate, TIPT, tetrabutyl titanate, tetrahexyl titanate, and tetraisooctyl titanate.

The polyol in step a) has a general formula of $R—(OH)_x$, where x≥2; and the polyol includes any one or a mixture of two or more selected from the group consisting of EG, DEG, TEG, tetraethylene glycol, 1,2-propanediol, 1,3-propanediol, 1,4-butanediol, 1,6-hexanediol, PEG 200, PEG 400, PEG 600, PEG 800, 1,4-cyclohexanediol, 1,4-CHDM, 1,4-benzenedimethanol, glycerol, trimethylolpropane, pentaerythritol, xylitol, and sorbitol.

Preferably, a molar ratio of the titanate to the polyol in step a) is:

$$Ti(OR)_4/R—(OH)_x=(0.8\text{-}1.2)x/4$$

Preferably, the reaction in step a) is conducted for 2 h to 10 h at 80° C. to 180° C. under nitrogen protection.

Preferably, a conversion rate of the transesterification reaction in step a) is 65% to 80%.

Preferably, the step b) is conducted under vacuum distillation at a vacuum degree of 0.05 KPa to 3 KPa.

Preferably, the reaction in step b) is conducted at 170° C. to 230° C. for 0.5 h to 5 h.

Preferably, a conversion rate of the transesterification reaction in step b) is greater than 90%.

Preferably, a molar ratio of the titanium-ester polymer to the terephthalic acid in step c) is: titanium-ester polymer: terephthalic acid=(0.5-2):1, where a mole number of the titanium-ester polymer is calculated based on a titanium content in the titanium-ester polymer; and the titanium content in the titanium-ester polymer is calculated based on a mole number of $TiO_2$.

Preferably, the organic solvent in step c) is a mixture of DMF and methanol, and a volume ratio of DMF to methanol meets the following condition:

DMF:methanol=(6–15):1.

Preferably, the stirring in step c) may be omitted, or the stirring may be conducted at 20° C. to 100° C. for 1 h to 50 h.

Preferably, the crystallization in step d) is conducted at 120° C. to 180° C. for 1 d to 15 d.

Preferably, the crystallization in step d) is conducted in a dynamic or static state.

Preferably, the MOF MIL-125 obtained in step e) has microporous structures with a narrow pore size distribution and less non-skeleton titanium.

Example 1

A specific preparation process was as follows: 5 g of tetraethyl titanate and 10 g of PEG 200 were added to a three-necked flask and thoroughly mixed, the three-necked flask was connected to a distillation device, nitrogen was introduced for protection, and a resulting mixture was subjected to a transesterification reaction for 5 h at 175° C. under stirring, where a conversion rate of the transesterification reaction was 75%; a water pump was connected to the device, and a resulting reaction system was subjected to vacuum distillation for 1 h at a vacuum degree of 3 KPa and a temperature of 200° C. to make the transesterification reaction more complete to obtain a titanium-PEG ester polymer, where a conversion rate of the transesterification reaction was 92%; 5 g of the titanium-PEG ester polymer, 5 g of terephthalic acid, 18 mL of DMF, and 2 mL of methanol were mixed and stirred for 2 h at room temperature, and a resulting mixture was then transferred to a stainless steel high-pressure reactor; the high-pressure reactor was sealed and placed in an oven that had been heated to 120° C., and crystallization was conducted for 2 d at an autogenous pressure; and after the crystallization was completed, a solid product was separated through centrifugation, washed with deionized water until neutral, and dried at 110° C. in air to obtain the microporous MOF MIL-125, which was denoted as A1.

Example 2

A specific preparation process was as follows: 5 g of tetraethyl titanate and 3.13 g of EG were added to a three-necked flask and thoroughly mixed, the three-necked flask was connected to a distillation device, nitrogen was introduced for protection, and a resulting mixture was subjected to a transesterification reaction for 5 h at 100° C. under stirring, where a conversion rate of the transesterification reaction was 70%; a water pump was connected to the device, and a resulting reaction system was subjected to vacuum distillation for 1 h at a vacuum degree of 3 KPa and a temperature of 170° C. to make the transesterification reaction more complete to obtain a titanium-EG ester polymer, where a conversion rate of the transesterification reaction was 90%; 3 g of the titanium-EG ester polymer, 2 g of terephthalic acid, 9 mL of DMF, and 1.2 mL of methanol were mixed and stirred for 2 h at room temperature, and a resulting mixture was then transferred to a stainless steel high-pressure reactor; the high-pressure reactor was sealed and placed in an oven that had been heated to 150° C., and crystallization was conducted for 15 d at an autogenous pressure; and after the crystallization was completed, a solid product was separated through centrifugation, washed with deionized water until neutral, and dried at 110° C. in air to obtain the MOF MIL-125, which was denoted as A2.

Example 3

A specific preparation process was as follows: 5 g of tetrabutyl titanate and 11.35 g of 1,4-benzenedimethanol were added to a three-necked flask and thoroughly mixed, the three-necked flask was connected to a distillation device, nitrogen was introduced for protection, and a resulting mixture was subjected to a transesterification reaction for 5 h at 160° C. under stirring, where a conversion rate of the transesterification reaction was 80%; a water pump was connected to the device, and a resulting reaction system was subjected to vacuum distillation for 1 h at a vacuum degree of 3 KPa and a temperature of 230° C. to make the transesterification reaction more complete to obtain a titanium-1,4-benzenedimethanol ester polymer, where a conversion rate of the transesterification reaction was 95%; 4 g of the titanium-1,4-benzenedimethanol ester polymer, 6.2 g of terephthalic acid, 20 mL of DMF, and 2.3 mL of methanol were mixed and stirred for 2 h at room temperature, and a resulting mixture was then transferred to a stainless steel high-pressure reactor; the high-pressure reactor was sealed and placed in an oven that had been heated to 170° C., and crystallization was conducted for 1 d at an autogenous pressure; and after the crystallization was completed, a solid product was separated through centrifugation, washed with deionized water until neutral, and dried at 110° C. in air to obtain the MOF MIL-125, which was denoted as A3.

The crystallization in Examples 1 to 3 was static crystallization.

Example 4

An MOF MIL-125 was prepared by the same method as in Example 1, and specific preparation conditions were different from Example 1 as in Table 1 and Table 2.

TABLE 1

Condition parameters for the preparation of a titanium-ester polymer

| No. | Titanate, polyol, and a molar ratio thereof | Reaction temperature | Reaction time | Temperature for vacuum distillation | Time for vacuum distillation | Vacuum degree for vacuum distillation |
|---|---|---|---|---|---|---|
| 1# | TIPT:glycerol = 2.4:0.6 | 80° C. | 10 h | 180° C. | 3 h | 0.01 KPa |
| 2# | Tetrahexyl titanate:pentaerythritol = 0.75:0.25 | 90° C. | 8 h | 210° C. | 2.5 h | 0.05 KPa |
| 3# | Tetraisooctyl titanate:1,2-propanediol = 0.8:0.2 | 120° C. | 4 h | 170° C. | 5 h | 5 KPa |
| 4# | Tetrahexyl titanate:1,4-cyclohexanediol = 0.7:0.3 | 180° C. | 2 h | 230° C. | 0.5 h | 1.5 KPa |

TABLE 2

| Conditions for synthesis of the MOF MIL-125 | | |
|---|---|---|
| No. | Titanium-ester polymer, terephthalic acid, and a molar ratio thereof; and organic solvents, and a volume ratio thereof | Temperature and time for crystallization |
| A4 | Terephthalic acid:1# = 1:1; and DMF:methanol = 10:1 | 100° C., 30 d |
| A5 | Terephthalic acid:2# = 1:0.9; and DMF:methanol = 12:1 | 120° C., 10 d |
| A6 | Terephthalic acid:3# = 1:0.7; and DMF:methanol = 13:1 | 200° C., 5 d |
| A7 | Terephthalic acid:4# = 1:0.5; and DMF:methanol = 9:1 | 180° C., 8 d |

The crystallization involved in Example 4 was dynamic crystallization conducted in a rotary oven. The temperature and time for crystallization were shown in Table 2, and a rotational speed of the rotary oven was 35 rpm.

Example 5

A specific preparation process was as follows: 5 g of tetraethyl titanate and 10 g of PEG 200 were added to a three-necked flask and thoroughly mixed, the three-necked flask was connected to a distillation device, nitrogen was introduced for protection, and a resulting mixture was subjected to a transesterification reaction for 5 h at 175° C. under stirring, where a conversion rate of the transesterification reaction was 75%; a water pump was connected to the device, and a resulting reaction system was subjected to vacuum distillation for 1 h at a vacuum degree of 3 KPa and a temperature of 200° C. to make the transesterification reaction more complete to obtain a titanium-PEG ester polymer, where a conversion rate of the transesterification reaction was 92%; in order to verify that the titanium-ester polymer obtained in the present application was resistant to hydrolysis and insoluble in water, 5 g of the titanium-PEG ester polymer, 5 g of terephthalic acid, 18 mL of DMF, 2 mL of methanol, and 0.5 g of water were mixed and stirred for 2 h at room temperature, and a resulting mixture was then transferred to a stainless steel high-pressure reactor; the high-pressure reactor was sealed and placed in an oven that had been heated to 120° C., and crystallization was conducted for 2 d at an autogenous pressure; and after the crystallization was completed, a solid product was separated through centrifugation, washed with deionized water until neutral, and dried at 110° C. in air to obtain the microporous MOF MIL-125, which was denoted as A8. The crystallization in this example was static crystallization.

Example 6

Phase Structure Analysis

The samples A1 to A8 in Examples 1 to 5 each were subjected to XRD analysis, with Example 1 as a typical representative. FIG. 1 shows an XRD pattern of the sample A1 prepared in Example 1, and it can be seen from the figure that the sample A1 is a microporous MOF MIL-125. Compared with an XRD pattern of a product synthesized by the existing technique, the XRD pattern of the microporous MOF MIL-125 synthesized by the present application has clear peaks with sharp peak shapes and without tailing, and has a flat baseline, indicating that the microporous MOF MIL-125 synthesized by the present application has a regular structure, no heterocrystals, and no amorphous products.

Test results of the other samples are only slightly different from the pattern of the sample A1 in Example 1 in the intensity of the diffraction peak, and all of these samples are microporous MOF MIL-125.

Example 7

Morphology Analysis

Figure 2:
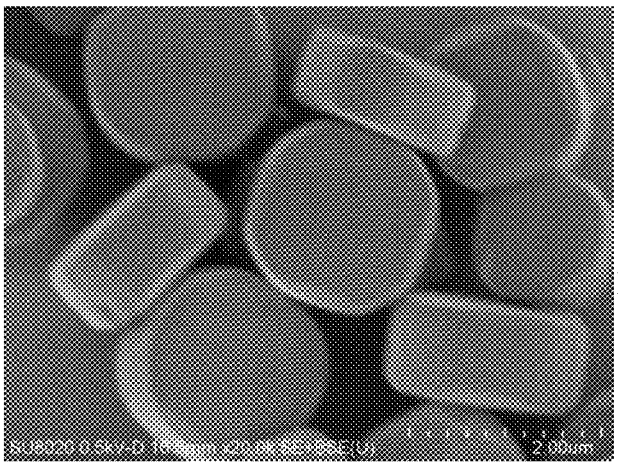
FIG. 2 is a scanning electron microscopy (SEM) image of the product synthesized in Example 1 of the present disclosure.

The samples A1 to A8 in Examples 1 to 5 each were subjected to SEM analysis, with Example 1 as a typical representative. FIG. 2 is an SEM image of the sample A1 prepared in Example 1, and it can be seen from the SEM image that the synthesized product has a regular morphology of a round cake shape and a uniform size distribution, and does not include other heterocrystals and amorphous products.

Example 8

Low-Temperature Nitrogen Physical Adsorption Analysis

Figure 3:
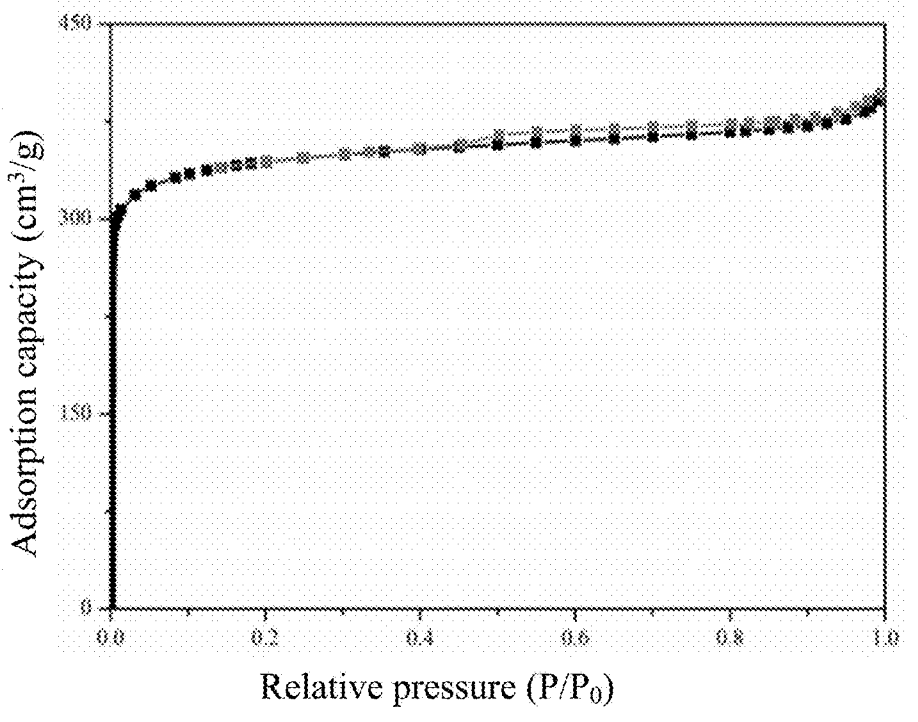
FIG. 3 is a physical adsorption isotherm (BET) of the product synthesized in Example 1 of the present disclosure.

The samples A1 to A8 in Examples 1 to 5 each were subjected to low-temperature nitrogen physical adsorption analysis, with Example 1 as a typical representative. FIG. 3 shows a physical adsorption isotherm of the sample A1 prepared in Example 1, and it can be seen from the figure that the isotherm is a typical type I adsorption isotherm, indicating a typical microporous structure.

Test results of the other samples are similar to the test results of the sample 1 in Example 1, and the samples each have a typical type I adsorption isotherm and a typical microporous structure.

Example 9

Pore Distribution Analysis

The samples A1 to A8 in Examples 1 to 5 each were subjected to physical adsorption and pore distribution analysis. Table 3 shows the physical adsorption and pore distribution results of the samples A1 to A6 prepared in Examples 1 to 4, and these samples each have an SSA of 1,200 $m^2/g$ to 1,350 $m^2/g$ and a micropore size of 0.37 nm to 0.48 nm.

TABLE 3

| SSA and pore distribution of samples | | | |
|---|---|---|---|
| Sample | BET SSA/ $m^2g^{-1}$ | t-Plot external SSA/$m^2g^{-1}$ | Pore distribution/nm |
| A1 | 1350 | 167 | 0.40 |
| A2 | 1268 | 170 | 0.37 |
| A3 | 1212 | 181 | 0.40 |
| A4 | 1304 | 165 | 0.41 |
| A5 | 1312 | 214 | 0.45 |
| A6 | 1289 | 200 | 0.48 |

Test results of the other samples are similar to the test results of the sample A1 in Example 1, and these samples each have an SSA of 1,000 $m^2/g$ to 1,500 $m^2/g$.

The external SSA of each of the samples was calculated by the t-Plot method. The samples A1 to A6 prepared in Examples 1 to 4 each have an external SSA of 160 $m^2/g$ to 214 $m^2/g$.

Test results of the other samples are similar to the test results of the sample A1 in Example 1, and these samples each have an external SSA of 160 $m^2/g$ to 220 $m^2/g$.

Example 10

Particle Size Distribution Analysis

Figure 4:
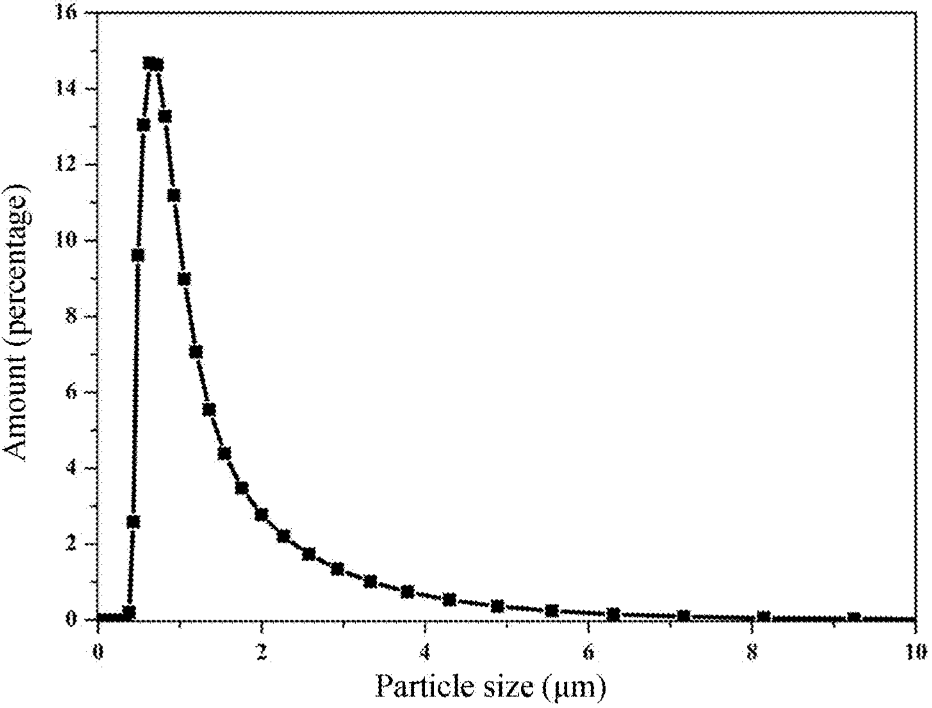
FIG. 4 shows a laser particle size distribution of the product synthesized in Example 1 of the present disclosure.

The samples A1 to A8 in Examples 1 to 5 each were subjected to laser particle size analysis, with Example 1 as a typical representative. FIG. 4 shows a particle size distribution of the sample A1 prepared in Example 1, and it can be seen from the figure that the particle size distribution of the synthesized sample is relatively concentrated and uniform and the particle size is 1 μm to 2 μm.

Test results of the other samples are similar to the test results of the sample 1 in Example 1, and these samples each have a relatively concentrated and uniform particle size distribution and a particle size of 1 μm to 2 μm.

Example 11

Determination of Oxidation Reaction Performance

Hydrogen peroxide was used as oxidizing agent to determine the performance of oxidizing cyclohexene.

With the sample A1 as a typical representative, the performance was specifically tested as follows:

0.1 g of the sample A1 (as a catalyst), 10 mL of acetonitrile, 0.36 g of cyclohexene, and 0.5 g of hydrogen peroxide (mass fraction: 30%) were added to a round-bottom flask, and heated in a 60° C. water bath for reflux condensation to allow a reaction for 4 h.

Reaction results of the sample A1 are as follows: cyclohexene conversion: 38%, selectivity for epoxidation products in the product: 78.5%, hydrogen peroxide conversion rate: 73.2%, and selectivity of the oxidizing agent for epoxidation products: 72.2%. In the prior art, the cyclohexene conversion rate is 26%, and the selectivity for epoxidation products in the product is only 25%.

The samples A2 to A8 each were subjected to performance analysis according to the above steps. Reaction results of these samples are similar to the reaction results of the sample A1.

The above examples are merely few examples of the present application, and do not limit the present application in any form. Although the present application is disclosed as above with preferred examples, the present application is not limited thereto. Some changes or modifications made by any technical personnel familiar with the profession using the technical content disclosed above without departing from the scope of the technical solutions of the present application are equivalent to equivalent implementation cases and fall within the scope of the technical solutions.

What is claimed is:

1. A metal-organic framework (MOF) MIL-125, wherein the MOF MIL-125 is as depicted in FIG. 2, the MOF MIL-125 has an external specific surface area (SSA) of 200 $m^2/g$ to 220 $m^2/g$ determined by a t-Plot method during a determination of physical adsorption, and a mass content of particles with a particle size of 1.6 μm to 1.8 μm in the MOF MIL-125 is 85% to 95%.

2. The MOF MIL-125 according to claim 1, wherein the MOF MIL-125 comprises a micropore with an SSA of 1,000 $m^2/g$ to 1,500 $m^2/g$.

3. The MOF MIL-125 according to claim 2, wherein the micropore has a pore size of 0.35 nm to 0.50 nm.

4. A preparation method of the MOF MIL-125 according to claim 1, comprising: preparing the MOF MIL-125 with a titanium-ester polymer, wherein the titanium-ester polymer is configured as a titanium source.

5. The preparation method according to claim 4, comprising: subjecting a mixture of the titanium-ester polymer, an organic ligand, and an organic solvent to a crystallization to obtain the MOF MIL-125, wherein the organic ligand is terephthalic acid; and the crystallization refers to a solvothermal crystallization.

6. The preparation method according to claim 5, wherein the crystallization is conducted for no more than 30 d at a temperature of 100° C. to 200° C. and an autogenous pressure under closed conditions.

7. The preparation method according to claim 5, wherein the crystallization is conducted for 1 d to 15 d at a temperature of 120° C. to 180° C. and an autogenous pressure under closed conditions.

8. The preparation method according to claim 5, wherein a molar ratio of the titanium-ester polymer to the organic ligand is (0.5-2):1;

a mole number of the titanium-ester polymer is calculated based on a titanium content in the titanium-ester polymer; and the titanium content in the titanium-ester polymer is calculated based on a mole number of $TiO_2$.

9. The preparation method according to claim 5, wherein the organic solvent is at least one selected from the group consisting of N,N-dimethylformamide (DMF) and methanol.

10. The preparation method according to claim 9, wherein the organic solvent comprises the DMF and the methanol, and a volume ratio of the DMF to the methanol is (6-15):1.

11. The preparation method according to claim 5, wherein the titanium-ester polymer is prepared through a transesterification reaction between a titanate and a polyol.

12. The preparation method according to claim 11, wherein the titanate is at least one selected from the group consisting of compounds with a chemical formula shown in formula II:

formula II

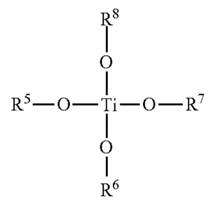

wherein $R^5$, $R^6$, $R^7$, and $R^8$ each are independently selected from the group consisting of $C_1$-$C_{10}$ alkyl groups; and the polyol comprises at least one selected from the group consisting of ethylene glycol (EG), diethylene glycol (DEG), triethylene glycol (TEG), tetraethylene glycol, 1,2-propanediol, 1,3-propanediol, 1,4-butanediol, 1,6-hexanediol, polyethylene glycol (PEG) 200, PEG 400, PEG 600, PEG 800, 1,4-cyclohexanediol, 1,4-cyclohexanedimethanol (1,4-CHDM), 1,4-benzenedimethanol, glycerol, trimethylolpropane, pentaerythritol, xylitol, and sorbitol.

13. A preparation method of epoxycyclohexane, comprising: subjecting a raw material comprising a compound A and cyclohexene to a reaction in a presence of the MOF MIL-125 according to claim 1 to obtain the epoxycyclohexane, wherein the compound A is at least one selected from the group consisting of hydrogen peroxide and tert-butyl hydroperoxide.

14. The preparation method according to claim 13, wherein the compound A, the cyclohexene, and the MOF MIL-125 are in a mass ratio of (0.3-1.0):(0.3-1.2):(0.05-0.1).

15. The preparation method according to claim 13, wherein the reaction is conducted at 35° C. to 80° C. for 2 h to 8 h.

16. The preparation method according to claim 4, wherein the MOF MIL-125 comprises a micropore with an SSA of 1,000 $m^2/g$ to 1,500 $m^2/g$.

17. The preparation method according to claim 16, wherein the micropore has a pore size of 0.35 nm to 0.50 nm.

* * * * *